US00PP19322P2

(12) United States Plant Patent
Hooijman

(10) Patent No.: US PP19,322 P2
(45) Date of Patent: Oct. 14, 2008

(54) *HYPERICUM* PLANT NAMED 'ESM PIN'

(50) Latin Name: *Hypericum androsaemum*
Varietal Denomination: Esm Pin

(75) Inventor: Aloysius A. J. Hooijman, Aalsmeer (NL)

(73) Assignee: ESmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 11/890,462

(22) Filed: Aug. 6, 2007

(51) Int. Cl.
*A01H 5/00* (2006.01)

(52) U.S. Cl. ..... Plt./226

(58) Field of Classification Search ..... Plt./226, Plt./263.1

See application file for complete search history.

*Primary Examiner*—Kent L Bell
(74) *Attorney, Agent, or Firm*—C. A. Whealy

(57) ABSTRACT

A new and distinct cultivar of *Hypericum* plant named 'Esm Pin', characterized by its compact, upright and uniform plant habit; vigorous growth habit; uniform and freely flowering habit; uniform and high density of fruits; large light red-colored fruits; and tolerant to wind and rain.

1 Drawing Sheet

Botanical designation: *Hypericum androsaemum.*
Cultivar denomination: 'Esm Pin'.

BACKGROUND OF THE INVENTION

The present invention relates to a new and distinct cultivar of *Hypericum,* botanically known as *Hypericum androsaemum* and hereinafter referred to by the name 'Esm Pin'.

The new *Hypericum* is a product of a planned breeding program conducted by the Inventor in El Quinche, Pichincha, Ecuador. The objective of the breeding program is to create new pot-type *Hypericum* cultivars with numerous attractive fruits.

The new *Hypericum* originated from a cross-pollination in February, 2000 in El Quinche, Pichincha, Ecuador of a proprietary selection of *Hypericum androsaemum* identified as code designation Line 58, not patented, as the female, or seed parent with a proprietary selection of *Hypericum androsaemum* identified as code designation Line 20, not patented, as the male, or pollen, parent. The new *Hypericum* was discovered and selected by the Inventor as a single flowering plant within the progeny of the stated cross-pollination in a controlled environment in El Quinche, Pichincha, Ecuador Asexual reproduction of the new cultivar by vegetative cuttings in El Quinche, Pichincha, Ecuador, since August, 2000, has shown that the unique features of this new *Hypericum* are stable and reproduced true to type in successive generations.

SUMMARY OF THE INVENTION

Plants of the cultivar Esm Pin have not been observed under all possible environmental conditions. The phenotype may vary somewhat with variations in environment such as temperature and light intensity without, however, any variance in genotype.

The following traits have been repeatedly observed and are determined to be the unique characteristics of 'Esm Pin'. These characteristics in combination distinguish 'Esm Pin' as a new and distinct cultivar of *Hypericum:*

1. Compact, upright and uniform plant habit.
2. Vigorous growth habit.
3. Uniform and freely flowering habit; uniform and high density of fruits.
4. Large light red-colored fruits.
5. Tolerant to wind and rain.

Plants of the new *Hypericum* differ from plants of the female parent selection in the following characteristics:

1. Plants of the new *Hypericum* are shorter than plants of the female parent selection.
2. Plants of the new *Hypericum* are more freely flowering than plants of the female parent selection.
3. Fruits of plants of the new *Hypericum* are narrower than fruits of plants of the female parent selection.

Plants of the new *Hypericum* differ from plants of the male parent selection in the following characteristics:

1. Plants of the new *Hypericum* are shorter than plants of the male parent selection.
2. Fruits of plants of the new *Hypericum* are narrower than fruits of plants of the male parent selection.
3. Plants of the new *Hypericum* and the male parent selection differ in fruit color as plants of the male parent selection have burgundy-colored fruits.

Plants of the new *Hypericum* can be compared to plants of the cultivar Bosapin, disclosed in U.S. Plant Pat. No. 10,933. In side-by-side comparisons conducted by the Inventor in El Quinche, Pichincha, Ecuador, plants of the new *Hypericum* differed from plants of the cultivar Bosapin in the following characteristics:

1. Plants of the new *Hypericum* were shorter and had shorter internodes than plants of the cultivar Bosapin.
2. Plants of the new *Hypericum* were more freely branching than plants of the cultivar Bosapin.
3. Plants of the new *Hypericum* flowered earlier than plants of the cultivar Bosapin.
4. Plants of the new *Hypericum* had smaller fruits than plants of the cultivar Bosapin.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the actual colors of the new *Hypericum*. The photograph comprises a side perspective view of a typical stem of 'Esm Pin' with mature fruits.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photograph and following description were grown under conditions which closely approximate commercial production conditions in an outdoor nursery in El Quinche, Pichincha, Ecuador for about 18 months. During production of the plants, day temperatures ranged from 12° C. to 30° C., night temperatures ranged from 5° C. to averaged 12° C. and light levels ranged from 1,000 to 1,150 foot-candles.

Botanical description: *Hypericum androsaemum* cultivar Esm Pin.

Parentage:

*Female, or seed, parent.*—Proprietary selection of *Hypericum androsaemum* identified as code designation Line 58, not patented.

*Male, or pollen, parent.*—Proprietary selection of *Hypericum androsaemum* identified as code designation Line 20, not patented.

Propagation:

*Type cutting.*—Vegetative cuttings.

*Time to initiate roots.*—About seven to ten days at 22° C. to 30° C.

*Time to produce a rooted young plant.*—About four to five weeks at 22° C. to 30° C.

*Root description.*—Thick, fibrous; color, 200B.

*Rooting habit.*—Freely branching; dense.

Plant description:

*Form.*—Compact, upright and uniform plant habit. Freely branching with about ten flowering stems developing per plant per year; dense and bushy plant form; vigorous growth habit. Typically grown as a pot-type *Hypericum*.

*Plant height.*—About 63 cm.

*Plant width* (*spread*).—About 34 cm.

*Lateral branch description.*—Length: About 60 cm. Diameter: About 4 mm. Internode length: About 4.8 cm. Strength: Strong. Texture: Smooth, glabrous. Color: 146D overlain with 166B.

Foliage description:

*Arrangement.*—Opposite, simple; sessile.

*Length.*—About 8 cm.

*Width.*—About 4.3 cm.

*Shape.*—Ovate.

*Apex.*—Obtuse.

*Base.*—Obtuse.

*Margin.*—Entire.

*Texture, upper and lower surfaces.*—Smooth, glabrous; leathery.

*Venation pattern.*—Pinnate.

*Color.*—Developing foliage, upper surface: Close to 143A. Developing foliage, lower surface: Close to 148B. Fully expanded foliage, upper surface: Close to 139A; venation, close to 144C. Fully expanded foliage, lower surface: Close to 138B; venation, 147D.

Flower description:

*Flower arrangement and shape.*—Bright yellow-colored single flowers arranged in terminal compound umbels; freely flowering with about nine flowers per umbel. Flowers not persistent. Flowers face mostly upright.

*Fragrance.*—Moderate.

*Natural flowering season.*—Year-round in Ecuador.

*Flower longevity.*—Flowers last about two to four days on the plant.

*Flower buds.*—Length: About 9 mm. Diameter: About 8 mm. Shape: Globose. Color: 14A.

*Inflorescence size.*—Length: About 11 cm. Diameter: About 15 cm.

*Flowers.*—Diameter: About 2.6 cm. Depth (height): About 1.2 cm.

*Petals.*—Quantity/arrangement: Five in a single whorl. Length: About 1.2 cm. Width: About 8 mm. Shape: Oval. Apex: Obtuse. Base: Attenuate. Margin: Entire. Texture, upper and lower surfaces: Glabrous, smooth; papery. Aspect: Incurved; concave. Color: When opening, upper surface: 13A. When opening, lower surface: 12A. Fully opened, upper surface: 14A; color becoming lighter than 14A with development. Fully opened, lower surface: 13B.

*Sepals.*—Quantity/arrangement: Five in a single whorl; three larger than the other two. Length: About 1.1 cm to 1.4 cm. Width: About 6 mm to 8 mm. Shape: Ovate to elliptic. Apex: Acute. Base: Attenuate. Margin: Entire. Texture, upper and lower surfaces: Glabrous, smooth. Aspect: Recurved. Color: When opening, upper surface: Close to 183A. When opening, lower surface: Close to 183B. Fully opened, upper surface: Close to 143A. Fully opened, lower surface: Close to 138C.

*Peduncles.*—Strength: Strong. Length: About 6.5 cm. Diameter: About 4 mm. Texture: Smooth, glabrous. Color: 166B.

*Pedicels.*—Strength: Moderately strong. Length: About 1.3 cm. Diameter: About 2 mm. Aspect: About 51° from the stem axis. Texture: Smooth, glabrous. Color: 178A.

*Reproductive organs.*—Stamens: Quantity per flower: About 100. Anther shape: Reniform. Anther length: About 1 mm. Anther color: Close to 13A. Pollen amount: Abundant. Pollen color: Close to 163B. Pistils: Quantity per flower: Single pistil with three stigmas. Pistil length: About 1 cm. Stigma shape: Circular. Stigma color: Close to 178A. Style length: About 4 mm. Style color: Close to 2B. Ovary color: Close to 1B.

*Fruits.*—Length: About 1 cm. Diameter: About 9 mm. Shape: Ovate. Texture: Smooth, glabrous. Color: Close to 46B to 46C; towards the base, 11C.

*Seeds.*—Length: About 0.1 mm. Diameter: About 0.03 mm. Color: Close to 200C.

Disease/pest resistance: Plants of the new *Hypericum* have not been noted to be resistant to pathogens and pests common to *Hypericum*.

Weather/temperature tolerance: Plants of the new *Hypericum* have been observed to tolerate wind, rain and temperatures ranging from about 0° C. to about 35° C.

It is claimed:

1. A new and distinct *Hypericum* plant named 'Esm Pin' as illustrated and described.

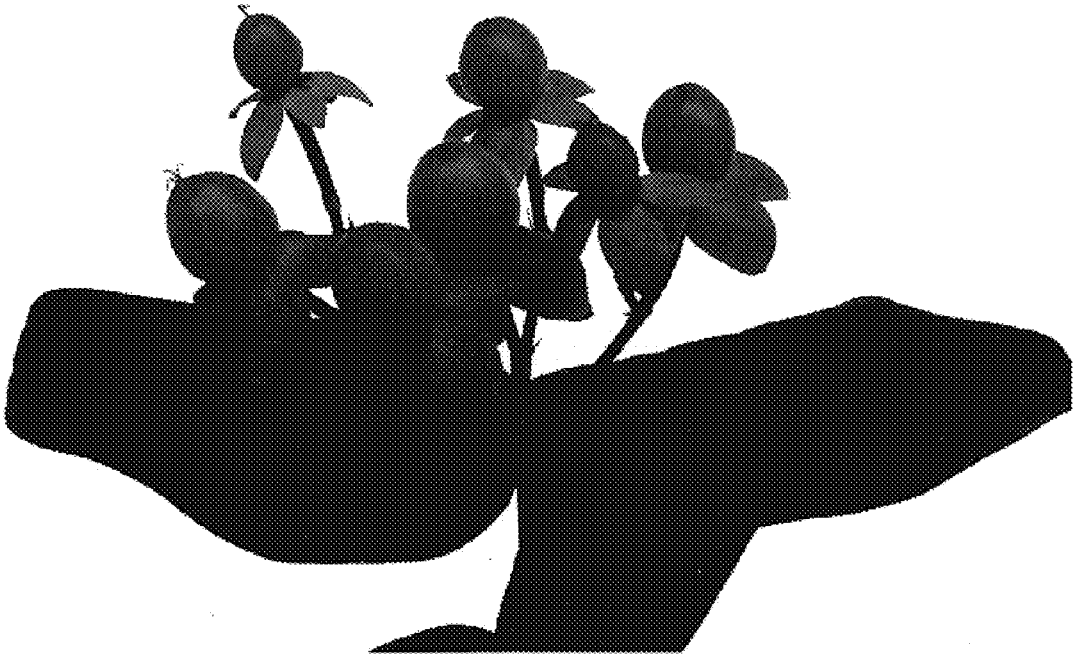

* * * * *